United States Patent [19]

Stokes

[11] Patent Number: 4,577,642
[45] Date of Patent: Mar. 25, 1986

[54] DRUG DISPENSING BODY IMPLANTABLE LEAD EMPLOYING MOLECULAR SIEVES AND METHODS OF FABRICATION

[75] Inventor: Kenneth B. Stokes, Minneapolis, Minn.

[73] Assignee: Medtronic, Inc., Minneapolis, Minn.

[21] Appl. No.: 706,215

[22] Filed: Feb. 27, 1985

[51] Int. Cl.$^4$ .............................................. A61N 1/04
[52] U.S. Cl. .............................. 128/784; 128/419 P; 128/786; 604/891
[58] Field of Search .................. 128/419 P, 784, 785, 128/786; 604/20, 21, 890, 891, 892, 893, 894

[56] References Cited

U.S. PATENT DOCUMENTS

| | | | |
|---|---|---|---|
| 4,351,337 | 9/1982 | Sidman | 604/891 |
| 4,352,360 | 10/1982 | King | 128/786 |
| 4,360,031 | 11/1982 | White | 128/786 |

FOREIGN PATENT DOCUMENTS 0047013  3/1982  European Pat. Off. ............ 128/786

Primary Examiner—William E. Kamm
Attorney, Agent, or Firm—Reed A. Duthler; Joseph F. Breimayer; John L. Rooney

[57] ABSTRACT

A body implantable lead for the delivery of stimulation energy to a desired body site including a drug dispenser carried by the lead which retains a drug to be dispensed while allowing the dispensing of that drug at least adjacent the desired body stimulation site. The drug is retained in a cavity within the lead, in the form of a solid plug or a powder wherein the drug is compounded with an appropriate molecular sieve material. The drug is released only after the molecular sieves are activated by exposure to water. In those embodiments in which the molecular sieves take the form of a powder, the molecular sieves and drug may be conveniently loaded into the electrode, after manufacture and prior to implant.

9 Claims, 3 Drawing Figures

DRUG DISPENSING BODY IMPLANTABLE LEAD EMPLOYING MOLECULAR SIEVES AND METHODS OF FABRICATION

CROSS REFERENCE TO COMMONLY ASSIGNED COPENDING APPLICATION

Reference is made to U.S. patent application Ser. No. 476,436 filed Mar. 17, 1983, now U.S. Pat. No. 4,506,680, by Kenneth Stokes for a Drug Dispensing Body Implantable Lead.

BACKGROUND OF THE INVENTION

This invention pertains to electrical stimulation leads in general, and to cardiac pacing leads in particular.

Electrical stimulation of the body for medical purposes is well known in the prior art. Examples of devices for this purpose include the cardiac pacemaker and neurostimulator. In the pacemaker context, as well as other body stimulation contexts, the stimulation is delivered to the desired body site by an electrode carrying lead.

Interactions between the lead and body can vitiate the desired effects of the stimulation. For example, biologic reactions may encourage fibrosis. In the pace-making context, fibrosis is believed to be a major factor in the increase in chronic stimulation threshold that is usually experienced. Also, trauma results in inflamation of the tissue to be stimulated. Such inflamation may alter the response of the tissue to the stimulation energy, both acutely and chronically.

Other interactions between the lead and body, while not directly affecting the response of the tissue to the stimulation energy, can result in the occurrence of undesirable events. In some circumstances where electrical body stimulation is indicated, the body portion to be stimulated is irritable. The placement of a lead may compound this irritability. For example, the placement of a pacemaking lead may induce a cardiac arrhythmia. The presence of the lead may also promote thrombus formation.

The interactions noted above have long been recognized and efforts made to ameliorate their consequences. For example, the lead may be configured to reduce mechanical trauma and the response of irritable tissue during lead placement. Materials may be selected for the lead body and electrodes to minimize fibrosis. However, lead configuration must take into account other factors such as the efficiency of the delivery of the stimulation energy, the ease of lead placement, maintenance of the desired electrode position and reliability of the lead over extended periods of time. An accommodation of these interests has resulted in leads whose configuration necessarily results in undesirable interactions between the lead and body.

It is known that thrombus formation may also be countered by the administration of suitable drugs. It is also known that a systemic treatment with steroids results in acute reduction in the stimulation threshold level. In particular, systemic use of glucocorticosteroids has been used to treat chronic exit block, a condition in which the stimulation threshold rises above the output level of the implanted pacemaker. However, long term systemic use of such steroids produces undesirable side effects.

Recently, sodium dexamethasone phosphate, an antiinflammatory glucocorticosteroid, has been successfully incorporated into a drug dispensing body implantable lead as described in the above referenced Stokes application. Local delivery of the drug, at the pacing site, avoids the undesirable side effects of systemic application.

SUMMARY OF THE INVENTION

The present invention provides a body implantable lead for the delivery of stimulation energy to a desired body site and methods of fabricating the lead. A drug dispenser carried by the lead includes a member for retaining the drug to be dispensed while allowing a dispensing of that drug at the desired body stimulation site. In the pacing context, the drug may be one intended to counter thrombus formation, fibrosis, inflamation, or arrhythmias, or any combination thereof, or to accomplish any desirable localized purpose. In a preferred embodiment as a cardiac pacing lead, the drug may be the sodium salt of dexamethasone phosphate, an antiinflammatory glucocorticosteroid which, when dispensed by a lead according to the present invention, results in a chronic reduction of pacing thresholds and improved sensed signal amplitudes. In the context of neurostimulation for pain relief, morphine would be a suitable drug for use in the invention. Most preferably, the lead carries a tip electrode at its distal end with the drug being dispensed through a porous, sintered elution path within the electrode. In some embodiments, it is desirable to additionally apply the drug to a porous portion of the tip electrode, adjacent the exit point of the elution path.

Because many drugs, including glucocorticosteroids, may lose effectiveness after prolonged periods of storage, or after exposure to excessive heat or light, manufacture of a drug dispensing electrode poses problems not encountered in the manufacture of a typical electrode lead. All manufacturing steps subsequent to insertion of the drug into the lead structure must be carried out at a temperature below the temperature at which the drug loses effectiveness. This factor virtually rules out the use of any steps in which the electrode is baked at high temperatures for a long period of time, and poses severe restraints on the use of welding to connect various electrode structures to one another. Further, if the drug is inserted during manufacture, the shelf life of the lead must be limited to the shelf life of the drug. In contrast, the shelf life of a typical electrode lead is limited only by the ability of its packaging to retain sterility.

In the present invention, the drug stored within the electrode is retained by molecular sieves, which control the rate of its elution. By variation of the molecular sieves, variable elution rates can be accomplished, without the need of varying the basic, mechanical structure of the pacing lead. This in itself is believed to be a substantial advantage over a system in which elution rate is controlled by means of mechanical variation of the electrode structure, for example by variation of porosity of a sintered elution path. In addition, by compounding the drug with the molecular sieve material, in the form of a powder, the drug may be loaded into the electrode after final assembly of the electrode, by means of a side bore, open to the interior cavity of the electrode. This approach, if used as the final manufacturing step, has the advantage of removing limitations as to baking or welding steps in the manufacture of the lead. Further, because the lead may be loaded with the drug after manufacture, it is thereby practical for the drug to be loaded into the electrode by the physician, shortly prior to implant, removing any drug imposed restrictions on the shelf life of the lead, and providing the physician with a degree of dosage control.

A final advantage is that the sieves themselves may be loaded into the lead during manufacture, and then loaded with the drug by the physician prior to implant by soaking the lead in a solution of the drug.

This invention, and its advantages, may be more fully understood in conjunction with the following detailed description.

DESCRIPTION OF THE INVENTION

DETAILED DESCRIPTION OF THE DRAWINGS

Figure 1:
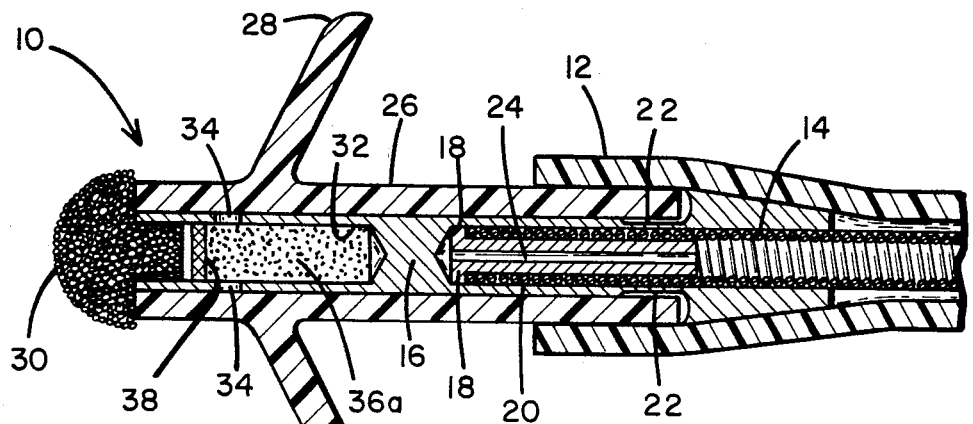
FIG. 1 illustrates a side sectional view of a preferred embodiment of the proximal portion of a pacing lead employing the present invention.

FIG. 1 illustrates a side sectional view of the proximal end of a lead according to the present invention. The proximal end of lead 10 is provided with a porous, sintered electrode 30, which is welded or crimped to an inner electrode member 16. Inner electrode member 16 is provided with a first bore 32, into which electrode 30 is crimped or welded, and is provided with a second bore 20, the function of which will be discussed below. Surrounding inner electrode member 16 is insulative sheath 26 which is provided with four tines 28, the function of which is described in U.S. Pat. No. 3,902,501 issued to Citron et al and incorporated herein by reference in its entirety. Insulative sheath 26 is preferably fabricated of silicone rubber, but may be fabricated of other, pliant insulative materials. Inner electrode member 16 is provided with two apertures 34, which extend from bore 32, to insulative sheath 26. After fabrication of the electrode, these apertures 34 may be used to load a powdered form of the molecular sieve material 36a. Additionally, after mounting pliant insulative sheath 26, a hypodermic needle or other sharpened tubular instrument may be used to pierce insulative sheath 26, in the vicinity of bore 34, in order to provide a path through which to introduce the desired drug, compounded with its molecular sieves, 36a. In this embodiment, silicone rubber is especially desirable as a material for sheath 26, in that it is generally self-sealing upon removal of the aforementioned needle. This procedure could be performed either by the physician or the manufacturer. If the particle size of powder 36a is smaller than the general pore size of sintered electrode 30, it is desirable to include within bore 32 of inner electrode member 16 a screen 38 having apertures smaller than the particle size of powder 36a, to prevent elution of the molecular sieves through electrode 30. In operation, upon implant, body fluids, including water enter bore 32 by means of porous, sintered electrode 30. The elution rate of the drug, out of powder 36a and into body fluid via porous electrode 30 may be controlled by appropriate choice of molecular sieve material. In a lead in which the drug is intended to reduce irritability, fibrosis, or other electrode related problems, the fact that the drug is dispensed directly through the electrode is believed to be beneficial. Dispensing of the drug at the stimulation site is also believed beneficial where the drug augments the function of the stimulation, as in the case of morphine dispensed adjacent a neurostimulation electrode. The proximal portion of inner electrode member 14 serves as the means for attachment of a coiled conductor, and pacing lead body, typical of those in the prior art. Within bore 20 is shown coiled conductor 14, which is maintained in firm electrical contact with inner electrode member 16 by means of internal swaging bore 18 and crimps 22, which tightly clamp coil 14 between inner electrode member 16 and the swaging core. Insulative sheath 12 extends from the distal portion of the lead, to an electrical connector, at the proximal end of the lead which may be constructed using techniques well known to the art.

One example of molecular sieves appropriate for use in the present invention is the class of crystaline alumino silicates known as zeolites. The chief characteristic of the zeolites is the openness of their framework, which defines open cavities of various dimensions. Zeolites having cavities ranging from 3 or less Å to 10 or more Å in diameter are available from the Linde Division of Union Carbide.

The cations within the framework create areas of strong electropositive charge within each cavity, which are attracted to polar molecules small enough to enter the cavities. In their hydrated forms, these cavities contain water molecules. However, the water of hydration may be removed by heating in a vacuum. In the dehydrated form, the zeolites become absorbents and adsorbents for gases and liquids. In the anhydrous state, if these molecules are brought in contact with polar molecules of appropriate size to enter the cavity, they will be retained in the cavity by electrostatic forces, allowing the molecular sieves to function as selective absorbents. Similarly, if the molecular sieves are brought into contact with larger molecules having polar portions small enough to enter the cavity, that portion of the molecule may be retained within the cavity, allowing the molecular sieve to function as a selective adsorbent.

When exposed to water, the highly polar water molecule displaces the less polar molecules absorbed within or adsorbed on the molecular sieve material. This provides a release mechanism especially valuable in the context of an implantable stimulation electrode. In particular, the prior drug dispensing electrodes, as described in the above Stokes application, required the use of water soluble drugs, as elution occurred as a result of diffusion through the body fluid. In the present invention, however, the displacement of the drug absorbed within or adsorbed on the molecular sieve provides a mechanism capable of dispensing even non-water soluble drugs. For example, some steroids are fat or soluble, but relatively insoluble in water. In particular, the steroid dexamethasone is such a drug.

In addition to the above advantages, it is believed that by appropriate choice of molecular sieve cavity size in relation to the size of the polar drug molecule or the polar group on the drug molecule, variable elution rates can be achieved. This would allow for a more controlled elution program than with a mechanical mechanism, such as a porous sintered elution path which must, of course, vary with manufacturing tolerances.

In the present invention, molecular sieves are used to both store and stabilize the desired drug. If the sieves are used as adsorbents, it is desirable to make the particles of sieve material as small as possible, to maximize surface area for adsorption, as is shown in the drawing of FIG. 1. If the sieves are intended to function as selective absorbents, the particles may be of a larger size, as illustrated in FIG. 2, below.

As an alternative to loading the molecular sieves with drug prior to insertion into the pacing lead, it may be possible to load the sieves into chamber 32, during the manufacturing process. If the drug chosen is soluble in nonpolar solvents, such as mineral oil, the physician could then soak the distal end of the lead in a concentrated solution of the drug dissolved in a nonpolar solvent, thereby loading the sieves with the drug at time of implant. This method would allow a more concentrated drug load than would be possible with other absorbent materials, because the molecular sieves will preferentially absorb the polar drug over the nonpolar solvent. In this case, the embodiment of FIG. 1 employing molecular sieve particles of small size may be preferable, allowing for a more rapid absorption or adsorption of the desired drug. In order to employ this technique, the physician should know what the pore and cavity sizes of the molecular sieves are, and what the size and configuration of the drug molecules he intends to use on it, so that efficient absorption or adsorption of the drug can take place.

In use, when the lead is placed in an environment where the porous electrode is in contact with body fluid, the body fluid enters the drug storage chamber, displacing the drug from the molecular sieves, and forcing it out of the electrode.

Figure 2:
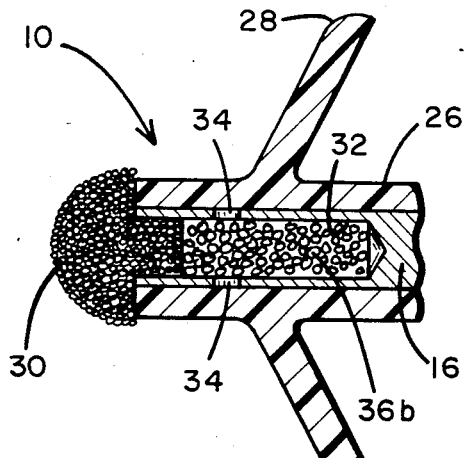
FIG. 2 illustrates a side sectional view of an alternate embodiment of the proximal portion of a lead according to the present invention.

FIG. 2 illustrates an alternate embodiment of the distal portion of a lead according to the present invention. All elements correspond to similarly numbered elements shown in FIG. 1. Powder 36b is shown as having a larger particle size, in order to indicate that in this embodiment, particle size of the powdered drug and molecular sieve material is greater than the pore size of porous electrode 30. This construction eliminates the need for a screen, 38, as is illustrated in FIG. 1. In all other respects, the functioning of the electrode according to FIG. 2 is identical to the electrode of FIG. 1. This electrode may similarly be loaded with the powder, subsequent to manufacturing and prior to implant by means of a needle inserted through insulative sheath 26 and bore 34.

Figure 3:
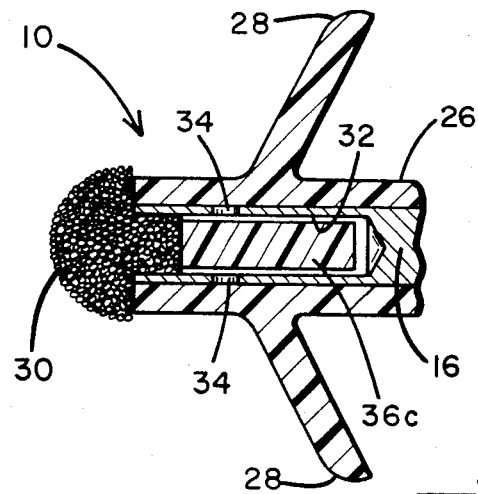
FIG. 3 illustrates a side sectional view of yet a third embodiment of the proximal portion of a lead employing the present invention.

FIG. 3 shows the proximal portion of yet a third embodiment of a lead according to the present invention. All numbered elements correspond to their similarly numbered elements shown in FIG. 1. In FIG. 3, however, the molecular sieve and drug are compounded into a solid plug, which is inserted during manufacture. In this embodiment, of course, care must be used in assembly and manufacture of the lead to avoid damage to the stored drug. However, this lead retains the advantage of allowing for variation in the elution rates of the stored drug, without the necessity of changing the porosity of sintered, porous electrode 30. As implanted, the electrode of FIG. 3 functions identically to the electrode of FIG. 1.

Other and further embodiments of the invention are readily apparent from the above description of the invention, and these embodiments are believed to be within the scope of the invention disclosed herein.

What is claimed is:

1. A body implantable electrode lead, comprising:
   an elongated insulative lead body having a proximal end and a distal end;
   an electrical conductor mounted within said lead body, having a proximal end and a distal end;
   an electrical connector mounted to the proximal end of said lead body and electrically coupled to said electrical conductor;
   electrode means for contacting body tissue along an exterior surface of said electrode, said electrode mounted to said lead body and electrically coupled to the proximal end of said electrical conductor, said electrode having a cavity therein open to said exterior surface; and
   dehydrated molecular sieve material mounted within said cavity.

2. A lead according to claim 1, further comprising:
   a polar drug adsorbed on said dehydrated molecular sieve material.

3. A lead according to claim 1, further comprising:
   a polar drug absorbed within said molecular sieve material.

4. A lead according to claims 1, 2 or 3 wherein said electrode has a bore connecting the cavity of said electrode to said exterior surface of said electrode.

5. A lead according to claim 4 further comprising retaining means for retaining said molecular sieve material within the cavity of said electrode.

6. A lead according to claim 5 wherein said retaining means comprises a porous material and wherein said molecular sieve material comprises a powder having particles larger than the pore size of said porous material.

7. A method of manufacturing an electrode, comprising the steps of:
   fabricating an electrode having an exterior surface, an internal cavity, a first bore extending from said cavity to said exterior surface, a retainer having pores mounted across said first bore, and a second bore connecting said cavity to the exterior of said electrode;
   dehydrating a molecular sieve material having a particle size larger than the pore size of said retainer; and
   loading said dehydrated molecular sieve material into said cavity via said second bore of said electrode.

8. A method according to claim 7 wherein said fabricating step includes providing said electrode with a layer of pierceable material extending over said second bore and wherein said loading step comprises piercing said pierceable material with a sharpened, tubular instrument having an internal bore and loading said molecular sieve particles via said internal bore.

9. A method of manufacturing an implantable electrode, comprising the steps of:
   fabricating an electrode having an internal cavity, an exterior surface, a first bore open to said exterior surface and to said internal cavity, a retainer having pores mounted across said bore and a dehydrated cavity containing molecular sieve material having particle size greater than the pore size of said retainer, mounted within said internal cavity of said electrode;
   dissolving a drug having a polar portion smaller than the cavity size of said molecular sieve material in a non-polar solvent; and
   soaking said electrode in said non-polar solvent in which said drug has been dissolved.

* * * * *